(12) United States Patent
Jeong

(10) Patent No.: US 9,690,031 B2
(45) Date of Patent: Jun. 27, 2017

(54) MOOD LAMP FOR VEHICLE

(71) Applicant: Hyundai Motor Company, Seoul (KR)

(72) Inventor: Byeong Ho Jeong, Seongnam-si (KR)

(73) Assignee: Hyundai Motor Company, Seoul (KR)

( * ) Notice: Subject to any disclaimer, the term of this patent is extended or adjusted under 35 U.S.C. 154(b) by 57 days.

(21) Appl. No.: 14/931,599

(22) Filed: Nov. 3, 2015

(65) Prior Publication Data

US 2016/0347243 A1 Dec. 1, 2016

(30) Foreign Application Priority Data

May 27, 2015 (KR) ........................ 10-2015-0073586

(51) Int. Cl.
| | |
|---|---|
| *B60Q 3/62* | (2017.01) |
| *F21V 8/00* | (2006.01) |
| *A61N 5/06* | (2006.01) |
| *B60Q 3/64* | (2017.01) |
| *B60Q 3/20* | (2017.01) |

(52) U.S. Cl.
CPC ......... *G02B 6/0031* (2013.01); *A61N 5/0618* (2013.01); *B60Q 3/20* (2017.02); *B60Q 3/64* (2017.02); *G02B 6/0021* (2013.01); *G02B 6/0025* (2013.01); *G02B 6/0043* (2013.01)

(58) Field of Classification Search
CPC ......... B60Q 3/54; B60Q 3/62; F21Y 2103/10; G02B 5/045; G02B 6/002; G02B 6/0028; G02B 6/0036; G02B 6/0043 G02B 6/0046; G02B 6/0051; G02B 6/0073
See application file for complete search history.

(56) References Cited

U.S. PATENT DOCUMENTS

| | | | | |
|---|---|---|---|---|
| 5,184,888 A | * | 2/1993 | Sakuma ................. | B60J 3/0282 296/97.2 |
| 8,233,117 B2 | * | 7/2012 | Nagata ................. | G02B 6/0028 349/105 |
| 8,432,353 B2 | * | 4/2013 | Nagata ................. | G02B 6/0028 345/102 |
| 8,534,896 B2 | * | 9/2013 | Boonekamp ......... | G02B 6/0063 362/607 |
| 8,911,133 B2 | * | 12/2014 | Sato ..................... | G02B 6/0061 362/607 |

(Continued)

FOREIGN PATENT DOCUMENTS

| | | |
|---|---|---|
| JP | 2012-048991 A | 3/2012 |
| KR | 20-0432241 Y1 | 11/2006 |

(Continued)

*Primary Examiner* — Hargobind S Sawhney
(74) *Attorney, Agent, or Firm* — Morgan Lewis & Bockius LLP

(57) ABSTRACT

A mood lamp may include a light source disposed at one side, a light guide panel transmitting and guiding light emitted from the light source to a front side, and a surface member disposed over a front surface of the light guide panel and having apertures for passing the light transmitted and guided by the light guide panel to the front side. The light guide panel may include optic protrusions formed on a rear surface of the light guide panel at locations corresponding to the apertures of the surface member and reflecting the light traveling through the light guide panel to the apertures. The light reflected by the optic protrusions is transmitted through the apertures of the surface member.

8 Claims, 4 Drawing Sheets

(56) References Cited

U.S. PATENT DOCUMENTS

| | | | |
|---|---|---|---|
| 8,998,466 B2* | 4/2015 | Wilfert | G02B 6/006 362/511 |
| 9,016,914 B2* | 4/2015 | Ukai | B60Q 3/004 362/488 |
| 2003/0128399 A1* | 7/2003 | Chino | B41J 2/445 358/296 |
| 2005/0276566 A1* | 12/2005 | Iimura | G02B 6/0018 385/146 |
| 2007/0025121 A1* | 2/2007 | Harada | G02B 5/0242 362/607 |
| 2007/0035958 A1* | 2/2007 | Mueller | B60Q 3/0283 362/488 |
| 2013/0335821 A1* | 12/2013 | Robinson | G02B 6/0023 359/464 |

FOREIGN PATENT DOCUMENTS

| | | |
|---|---|---|
| KR | 10-0704505 B1 | 4/2007 |
| KR | 10-1276627 B1 | 6/2013 |
| KR | 10-2014-0047963 A | 4/2014 |
| KR | 10-1440688 B1 | 9/2014 |
| WO | WO 2010/005655 A3 | 1/2010 |
| WO | WO 2010/005810 A3 | 1/2010 |

* cited by examiner

MOOD LAMP FOR VEHICLE

CROSS-REFERENCE TO RELATED APPLICATION

The present application claims priority of Korean Patent Application Number 10-2015-0073586 filed May 27, 2015, the entire contents of which application are incorporated herein for all purposes by this reference.

BACKGROUND

Technical Field

The present invention relates to a mood lamp for a vehicle. More particularly, the present invention relates to a mood lamp for a vehicle, which may implement an emotional illumination effect of the mood lamp using only a minimum number of Light Emitting Diodes (LEDs), may achieve simplification of the assembly process and cost saving in accordance with the reduction of the number of LEDs, and may overcome a limitation in regard to packaging due to installation of LEDs.

Background Art

Generally, vehicles are equipped with various kinds of lamps which illuminate the front side or the interior of vehicles. Recently, as the preferences of users are diversified, the cases where users install mood lamps inside vehicles increase.

The mood lamp is an interior lamp that is installed so as to satisfy the emotion of a user through various illumination effects inside a vehicle, and is configured by disposing small-sized lamps such as Light Emitting Diodes (LEDs) in a broad panel or board in various forms.

The mood lamp may be installed in various places inside a vehicle to create an atmosphere. For example, the mood lamp may be installed in a head lining to satisfy the emotion of a user through the mood illumination of the head lining.

FIG. 1 is a view illustrating a configuration of a typical mood lamp. In FIG. 1, the mood lamp in which a plurality of LEDs 2 are mounted onto a Printed Circuit Board (PCB) 1 is installed in a vehicle interior material, for example, in a head lining 3 that is an interior material of the indoor ceiling. Thus, light emitted from the LEDs 2 disposed at certain places inside the head lining 3 is emitted through apertures 4 of the head lining 3, implementing the mood illumination.

In this case, the LEDs 2 are located at different places between apertures 4 for a change of brightness according to the view angle in order to generate differences of the amount of light passing through the apertures 4. Thus, a twinkling effect can be implemented in accordance with the viewing angle by allowing a user to feel differences of twinkling degrees when viewing from left, center, and right.

However, since the mood illumination has to be implemented by installing the LEDs 2 at every aperture 2, there is an inconvenience in that LEDs need to be assembled one by one, and there is a limitation in that the manufacturing cost increases because a plurality of LEDs and PCBs are used.

Also, there is a limitation in regard to packaging due to the rear side installation of LEDs, and much time is taken and difficulties occur to manage the LEDs one by one.

The information disclosed in this Background section is only for enhancement of understanding of the general background of the invention and should not be taken as an acknowledgement or any form of suggestion that this information forms the prior art already known to a person skilled in the art.

SUMMARY OF THE DISCLOSURE

The present invention provides a mood lamp for a vehicle, which may implement an emotional illumination effect of the mood lamp using only a minimum number of Light Emitting Diodes (LEDs), may achieve simplification of the assembly process and cost saving in accordance with the reduction of the number of LEDs, and may overcome a limitation in regard to packaging due to installation of LEDs.

In one aspect, the present invention provides a mood lamp including: a light source disposed at one side thereof; a light guide panel transmitting and guiding light emitted from the light source to a front side; and a surface member disposed over a front surface of the light guide panel and having apertures for passing the light transmitted and guided by the light guide panel to the front side, wherein the light guide panel comprises optic protrusions formed on a rear surface of the light guide panel at locations corresponding to the apertures of the surface member and reflecting the light traveling through the light guide panel to the apertures, and the light reflected by the optic protrusions is transmitted through the apertures of the surface member.

In an exemplary embodiment, the light source may be disposed at an end of a side portion formed at one side of the light guide panel.

In another exemplary embodiment, the light guide panel may have an incidence groove formed at the end of the side portion that is convex at the one side of the light guide panel, and the light source may be disposed in the incidence groove.

In still another exemplary embodiment, the incidence groove may have an inner side surface formed in a parabolic shape such that the light emitted from the light source is diffused after incidence into the side portion of the light guide panel.

In yet another exemplary embodiment, an end surface of the side portion at the one side of the light guide panel may be formed in a parabolic shape such that the light incident into the side portion of the light guide panel from the light source in the incidence groove may be reflected into the light guide panel.

In still yet another exemplary embodiment, the optic protrusions may have a polyhedral shape with a plurality of faces to reflect light incident from an inside of the light guide panel to the light guide panel.

In a further exemplary embodiment, the optic protrusions may have a hexahedral shape.

In another further exemplary embodiment, the optic protrusions may be formed on the rear surface of the light guide panel and have different angles and rotation shapes.

Other aspects and exemplary embodiments of the invention are discussed infra.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
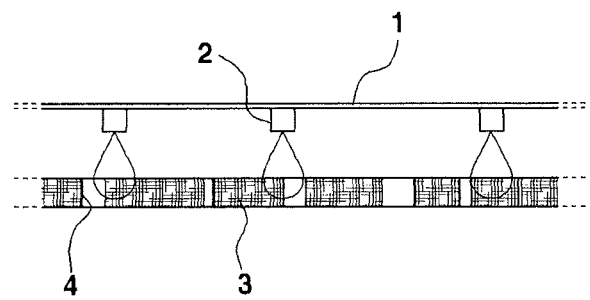
FIG. 1 is a view illustrating a configuration of a typical mood lamp.

Reference numerals set forth in the Drawings includes reference to the following elements as further discussed below:

| | |
|---|---|
| 3: head lining | 10: mood lamp |
| 11: light source (LED) | 12: light guide panel |
| 13: side portion | 13a: incidence groove |
| 13b: end surface of side portion | 14: optic protrusion |
| 15: surface member | 16: aperture |

It should be understood that the accompanying drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

Hereinafter, exemplary embodiments of the present invention will be described in detail with reference to the accompanying drawings so that those skilled in the art can easily carry out the present invention.

Figure 2:
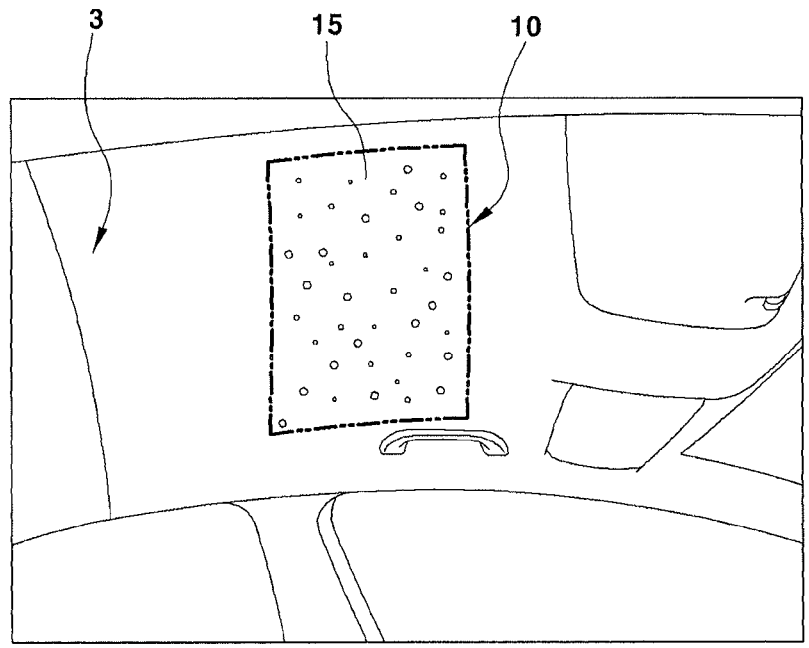
FIG. 2 is a view illustrating an installation location of a mood lamp according to an embodiment of the present invention.
Figure 3:
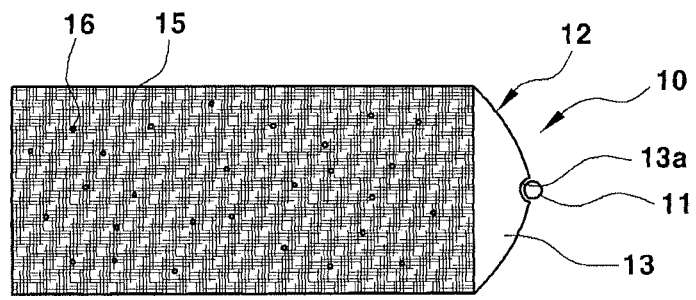
FIG. 3 is a front view illustrating a mood lamp according to an embodiment of the present invention.
Figure 4:
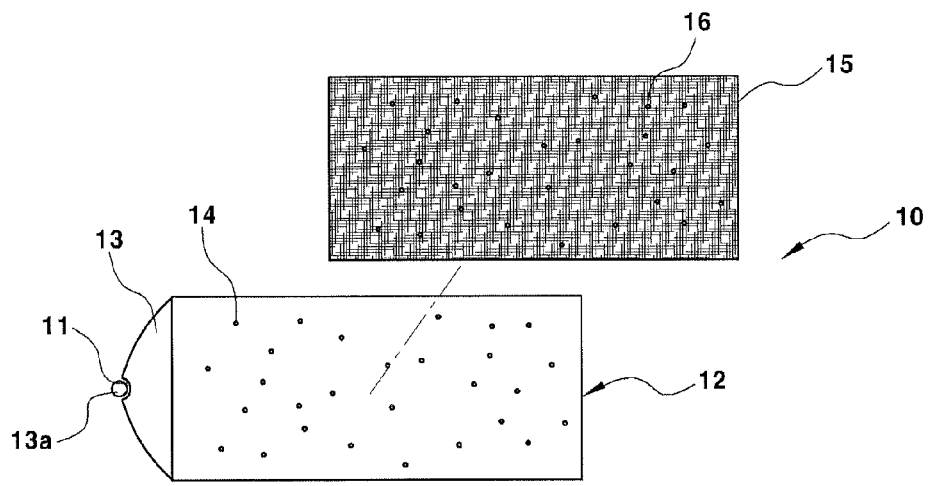
FIG. 4 is an exploded view illustrating a configuration of a mood lamp according to an embodiment of the present invention.

FIG. 2 is a view illustrating an installation location of a mood lamp according to an embodiment of the present invention. FIG. 3 is a front view illustrating a mood lamp according to an embodiment of the present invention. FIG. 4 is an exploded view illustrating a configuration of a mood lamp according to an embodiment of the present invention.

Figure 5:
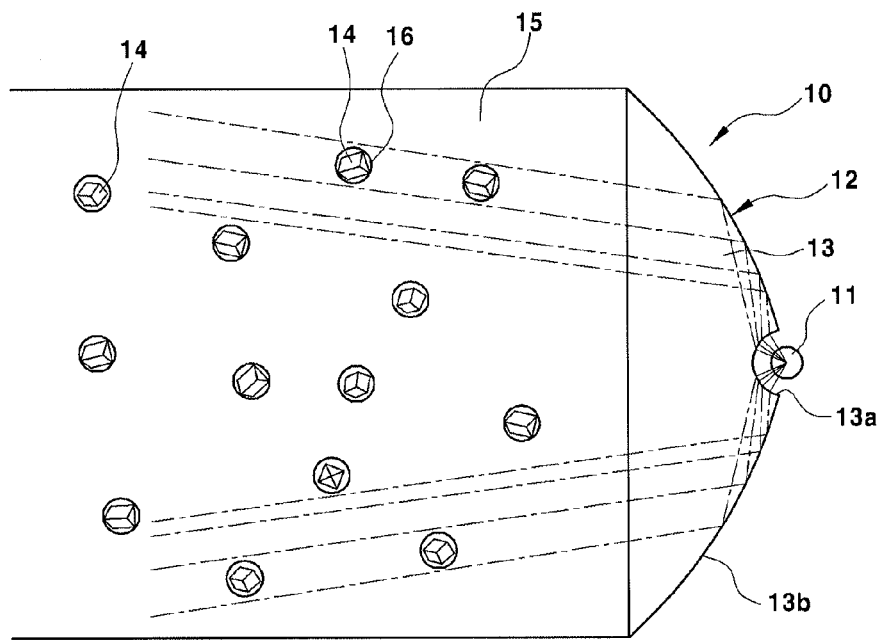
FIG. 5 is a front view illustrating a path of light in a mood lamp according to an embodiment of the present invention.
Figure 6:
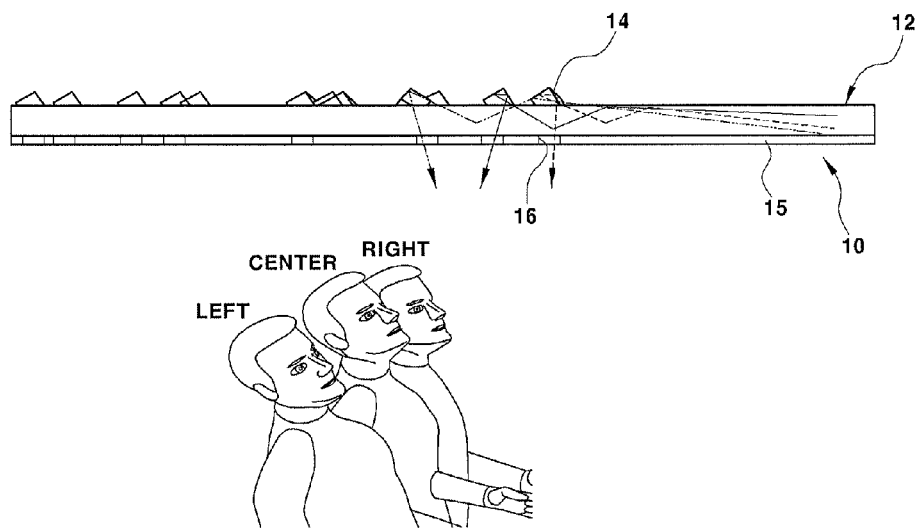
FIG. 6 is a cross-sectional view illustrating a path of light in a mood lamp according to an embodiment of the present invention.
Figure 7:
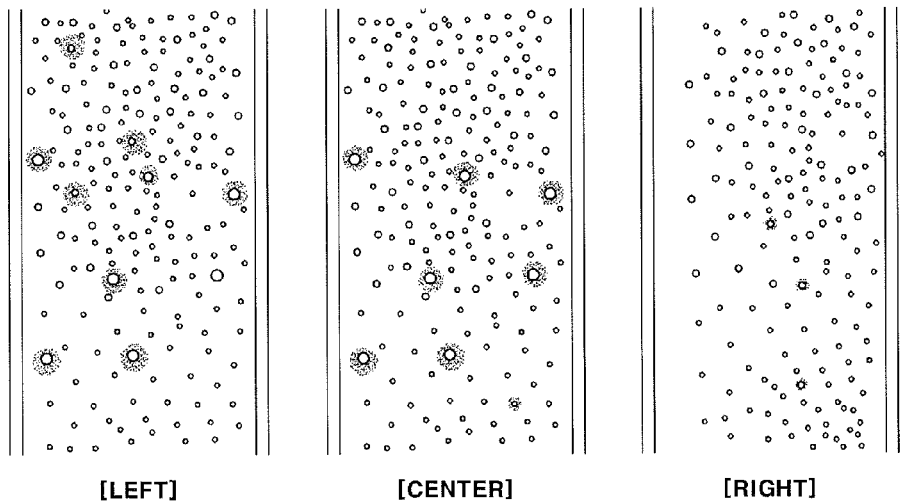
FIG. 7 is a view illustrating illumination states of a mood lamp with different appearance for each seating condition according to an embodiment of the present invention.

FIG. 5 is a front view illustrating a path of light in a mood lamp according to an embodiment of the present invention. FIG. 6 is a cross-sectional view illustrating a path of light in a mood lamp according to an embodiment of the present invention. FIG. 7 is a view illustrating illumination states of a mood lamp differently appearing for each seating condition according to an embodiment of the present invention.

A mood lamp 10 according to an embodiment may be disposed in (e.g., in, at or on) a vehicle interior material, and may be configured to show different illumination states in accordance with the viewing angle while using a single light source.

As shown in FIG. 2, the mood lamp 10 may be disposed in a head lining 3 that is an interior material of the indoor ceiling of a vehicle, and may be disposed in a predetermined portion of the head lining 3.

In this case, the mood lamp 10 may be configured to implement various twinkling effects according to the seating state, by allowing a user to feel differences of brightness degrees (twinkling degrees) of light appearing at each location (location of aperture) in accordance with differences between viewing angles due to the seating state, i.e., the seating location or seating position of a driver or a passenger sitting on a seat.

As shown in the drawings, the mood lamp 10 may include a light source 11 at one side thereof, a light guide panel 12 that is attached to the rear surface (inner side surface) of a surface member 15 and transmits and guides light emitted from the light source 11 to emit light to the front side, and a surface member 15 that is disposed at the front surface of the light guide panel 12 and has a plurality of apertures 16 for passing light emitted through the light guide panel 12 toward the front side.

In this configuration, one light source 11 disposed at one side of the light guide panel 12 may be used, and the light source 11 may include a Light Emitting Diode (LED).

Also, when the mood lamp 10 is installed at one side of the indoor head lining 3, the surface member 15 may become a portion of the whole head lining 3, and may have the plurality of apertures 16 for passing light.

The surface member 15 may be manufactured using the same material or color as the other portion of the head lining 3 around the mood lamp 10, and may be manufactured by forming the aperture 16 of a certain diameter (e.g., about 2 mm) in a non-woven fabric that is a typical material of the head lining 3.

The light guide panel 12 may be disposed on the rear surface of the head lining 3, e.g., the surface member 15 having the apertures 16 formed therein, and is assembled such that the head lining that is the surface member 15 can cover the front surface of the light guide panel 12.

The light guide panel 12 may be manufactured using a light transmittable material, and may be manufactured using a transparent resin, e.g., transparent acrylic resin that is injection-molded.

The light guide panel 12 may have an incidence groove 13a formed at one side portion 13 thereof. The light source 11 may be disposed in the incidence groove 13a. In this case, the inner side surface of the incidence groove 13a, e.g., an incidence surface of light to which light emitted from the light source 11 is incident may be formed to have a parabolic shape such that light emitted from the light source 11 can be uniformly or more evenly diffused into the light guide panel 12 at a wide angle.

Also, an end surface 13b of the side portion 13 of the light guide panel 12 around the incidence groove 13a where the light source 11 is located may be formed to have a shape that can reflect a larger amount of light incident to the incidence groove 13a and diffused into the light guide panel 12. Similarly to the incidence groove 13a, the end surface 13b may be formed to have a parabolic shape.

In this case, the inner side surface of the incidence groove 13a and the end surface 13b of the side portion 13 of the light guide panel 12 may be formed to have a parabolic shape of an inverse direction to each other.

Also, the optic protrusion 14 for light reflection may be protrusively formed at every location corresponding to each aperture of the surface member 15. The optic protrusion 14 may be formed on the rear surface of the light guide panel 12 that serves to transmit and guide light and is injection-molded. The optic protrusion 14 of the light guide panel 12 may have a polyhedral shape.

In an exemplary embodiment, the shape of the optic protrusion 14 may be a hexahedral shape, and the polyhedral optic protrusions 14 may be formed to have various angles on the light guide panel 12.

When the polyhedral optic protrusions 14 are formed to have different angles, the different twinkling effects may be implemented according to the viewing angle.

Figure 8:
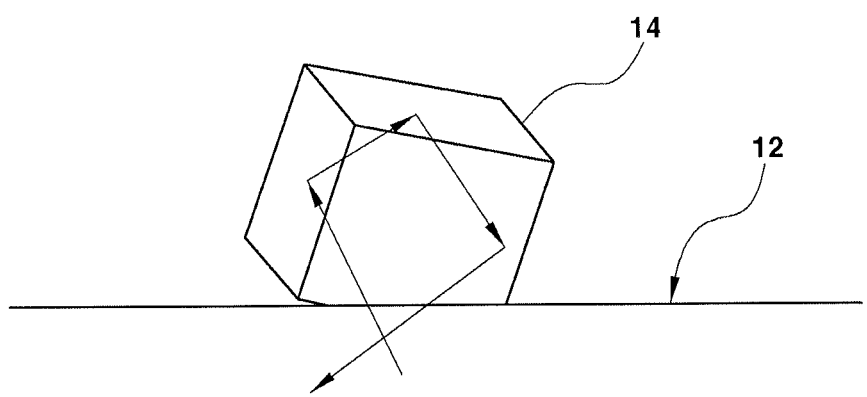
FIG. 8 is a view illustrating a reflection state of light by an optic protrusion having a hexahedral shape in a mood lamp according to an embodiment of the present invention.

FIG. 8 is a view illustrating light reflection by an optic protrusion having a hexahedral shape in a mood lamp according to an embodiment of the present invention. As shown in FIG. 8, regardless of the direction of light incident from the inside of the light guide panel 12 to the hexahedral optic protrusion 14, light may be reflected by the respective faces of the optic protrusion 14, and then may be again directed to the direction of the light guide panel 12 to which light is incident. In this case, light incident in a specific direction may be reflected by the respective faces and then emitted at a predetermined angle.

Accordingly, when the angles and the rotation shapes of the hexahedral optic protrusions 14 protruding from the rear surface of the light guide panel 12 are different from each other, the optic protrusions 14 may reflect light to or direct light at different angles. Consequently, in external appearance of the surface member 15, the degrees of the brightness (twinkling) of light passing the aperture 16 of the surface member 15 after reflected by each optic protrusion 14 may look different to each other.

In the mood lamp described above, the traveling path of light emitted from the light source may be described as follows with reference to FIGS. 5 and 6.

As shown in FIG. 5, the incidence groove 13a may be formed at the end of the side portion 13 that is convex at one side of the light guide panel 12, and the light source 11 may be disposed in the incidence groove 13a.

In this case, light emitted from the light source 11 inside the incidence groove 13a may be incident to the incidence surface having a parabolic shape and then may be diffused at a wide angle. Thereafter, light may be incident into the side portion 13 of the light guide panel 12, and then may be reflected by the end surface 13b of the side portion 13 of the light guide panel 12 to enter the light guide panel.

Thereafter, light may travel along the inside of the light guide panel 12 to be diffused and guided throughout the whole region of the light guide panel 12, and then may be reflected by the optic protrusions 14 formed at each location to pass the aperture 16 of the surface member 15.

In this case, since the optic protrusions 14 having a polyhedral (in some embodiments, preferably hexahedral) shape protrude from the rear surface of the light guide panel 12 at different angles and rotation shapes, the reflection directions and angles of light reflected by the optic protrusions 14 may be different from each other.

Thus, due to differences between the directions and angles of light reflected by the optic protrusions 14, the degrees of brightness (twinkling) of light emitted from the apertures 16 may look different to each other, and particularly, the illumination state may be changed due to the differences of the degrees of brightness of each aperture 16 in accordance with the viewing angle.

In other words, when light reflected by each optic protrusion 14 indoor at night passes the apertures 16 of the surface member 15, an illumination effect that light looks like stars having different degrees of brightness in the night sky is shown in external appearance of the surface member 15. Particularly, an illumination effect that the brightness of each aperture 16 changes in accordance with the viewing angle of a driver or a passenger may be shown.

FIG. 7 is a view illustrating different illumination effects at different viewing angles due to the seating location or the seating position, e.g., the seating state of a driver or a passenger. When the mood lamp 10 is viewed from left, center, and right locations, the illumination states may be different from each other in external appearance of the surface member 15 as exemplified in FIG. 7.

In a mood lamp according to an embodiment of the present invention, an emotional illumination effect of the mood lamp may be implemented using only one LED unlike a typical configuration in which LEDs need to be installed at every aperture.

Accordingly, the LED assembly process is simplified, and the cost necessary for LEDs may be reduced. Also, a typical large area PCB needed to install a plurality of LEDs is unnecessary, the effect of cost saving may be maximized.

Also, since one LED is disposed at the end of the side portion of a light guide panel unlike a related-art in which a large area PCB mounted with a plurality of LEDs is disposed at a rear side of a head lining (LEDs are not disposed at the rear side of the head lining), the present invention is more advantageous in regard to packaging for the installation of the mood lamp.

For convenience in explanation and accurate definition in the appended claims, the terms "left" or "right", "front" or "rear", and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A mood lamp comprising:
a light source disposed at one side thereof;
a light guide panel transmitting and guiding light emitted from the light source to a front side; and
a surface member disposed over a front surface of the light guide panel and having apertures for passing the light transmitted and guided by the light guide panel to the front side,
wherein the light guide panel comprises optic protrusions formed on a rear surface of the light guide panel at locations corresponding to the apertures of the surface member and reflecting the light traveling through the light guide panel to the apertures, and the light reflected by the optic protrusions is transmitted through the apertures of the surface member.

2. The mood lamp of claim 1, wherein the light source is disposed at an end of a side portion formed at one side of the light guide panel.

3. The mood lamp of claim 2, wherein the light guide panel has an incidence groove formed at the end of the side portion that is convex at the one side of the light guide panel, and the light source is disposed in the incidence groove.

4. The mood lamp of claim 3, wherein the incidence groove has an inner side surface formed in a parabolic shape such that the light emitted from the light source is diffused after incidence into the side portion of the light guide panel.

5. The mood lamp of claim 3, wherein an end surface of the side portion at the one side of the light guide panel is formed in a parabolic shape such that the light incident into the side portion of the light guide panel from the light source in the incidence groove is reflected into the light guide panel.

6. The mood lamp of claim 1, wherein the optic protrusions have a polyhedral shape with a plurality of faces to reflect light incident from an inside of the light guide panel to the light guide panel.

7. The mood lamp of claim 6, wherein the optic protrusions have a hexahedral shape.

8. The mood lamp of claim 6, wherein the optic protrusions are formed on the rear surface of the light guide panel and have different angles and rotation shapes.

* * * * *